(12) United States Patent
Wang

(10) Patent No.: US 9,724,463 B2
(45) Date of Patent: Aug. 8, 2017

(54) FLUID DISPENSING OR FEEDING DEVICE

(71) Applicant: Hong Jen Wang, Kaohsiung (TW)

(72) Inventor: Hong Jen Wang, Kaohsiung (TW)

(*) Notice: Subject to any disclaimer, the term of this patent is extended or adjusted under 35 U.S.C. 154(b) by 752 days.

(21) Appl. No.: 14/260,529

(22) Filed: Apr. 24, 2014

(65) Prior Publication Data

US 2015/0306308 A1     Oct. 29, 2015

(51) Int. Cl.
*A61M 5/168* (2006.01)
*F16K 31/08* (2006.01)
*F16K 31/06* (2006.01)
*A61M 5/142* (2006.01)
*A61M 5/14* (2006.01)

(52) U.S. Cl.
CPC .... *A61M 5/16813* (2013.01); *A61M 5/14216* (2013.01); *A61M 5/16831* (2013.01); *F16K 31/0651* (2013.01); *F16K 31/0686* (2013.01); *F16K 31/082* (2013.01); *A61M 5/14* (2013.01); *A61M 5/168* (2013.01); *A61M 5/16804* (2013.01); *A61M 5/16809* (2013.01)

(58) Field of Classification Search
CPC .............. A61M 5/142; A61M 5/14216; A61M 5/16804; A61M 5/16813; A61M 5/16831; A61M 5/16809; A61M 5/168; A61M 5/14; F16K 31/0651; F16K 31/0606; F16K 31/0686; F16K 31/08; F16K 31/082
See application file for complete search history.

(56) References Cited

U.S. PATENT DOCUMENTS

| 4,629,099 A | * | 12/1986 | Jones | A61M 5/142 137/614.2 |
| 5,556,263 A | * | 9/1996 | Jacobsen | A61M 5/142 417/490 |
| 7,455,658 B2 | | 11/2008 | Wang | |
| 7,516,873 B2 | | 4/2009 | Wang | |
| 7,584,872 B2 | | 9/2009 | Wang | |
| 8,348,106 B2 | | 1/2013 | Wang | |

* cited by examiner

*Primary Examiner* — Imani Hayman
*Assistant Examiner* — Nilay Shah
(74) *Attorney, Agent, or Firm* — Charles E. Baxley

(57) ABSTRACT

A fluid dispensing device includes a container coupled between a bottle and a discharge tube for forcing the fluid to flow through the discharge tube without gravity, a base member is disposed in the container, a housing is engaged in the container and movable toward and away from the base member, a spring biased plug controls the fluid to flow out of the housing, a cap and a casing are attached to the container, a spring biased valve piece is engaged in the casing for engaging with the cap and for controlling the fluid to flow through the cap, a magnetic member is attached to the casing, and a coil is attached to the container to act with and to move the magnetic member in the container.

10 Claims, 5 Drawing Sheets

FLUID DISPENSING OR FEEDING DEVICE

BACKGROUND OF THE INVENTION

1. Field of the Invention

The present invention relates to a fluid dispensing or feeding device, and more particularly to a fluid dispensing or feeding device including a pressurizing device for pressurizing a fluid and for allowing a fluid bottle to be disposed below hearts of patients or users, and thus for allowing the fluid dispensing or feeding device to be easily carried by the patients or users.

2. Description of the Prior Art

Typically, fluid dispensing or feeding devices have been developed and provided for feeding or injecting medicinal fluids intravenously into human body tissue, and comprise a feed tube having a hypodermic needle provided on one end thereof for engaging into a fluid bottle or container, and having an injection needle provided on the other end thereof, for penetrating into patient's body tissue and for the purposes of injecting the fluid as desired.

For example, U.S. Pat. No. 7,455,658 to Wang, U.S. Pat. No. 7,516,873 to Wang, U.S. Pat. No. 7,584,872 to Wang, and U.S. Pat. No. 8,348,106 to Wang were all developed by the present applicant and disclose several examples of the fluid dispensing devices each also including a pressurizing device coupled between a bottle and a discharge tube for forcing the fluid to flow through the discharge tube without gravity, in which the pressurizing device includes a container coupled between the bottle and the discharge tube, a piston slidably received in the container, and a motor coupled to the piston to move the piston in the reciprocating action within the container.

However, the piston may not be suitably actuated or operated by the motor to effectively pump or pressurize the fluid, or the fluid may not be effectively pumped or pressurized to feed or to inject into the user and an improved pressurizing device is further required to be developed and provided to pump or pressurize and to feed or to inject the fluid into the user.

The present invention has arisen to mitigate and/or obviate the afore-described disadvantages of the conventional fluid dispensing or feeding devices.

SUMMARY OF THE INVENTION

The primary objective of the present invention is to provide a fluid dispensing or feeding device including a pressurizing device for pressurizing a fluid and for allowing the fluid bottle to be disposed below hearts of patients or users, and thus for allowing the fluid dispensing or feeding device to be easily carried by the patients or users.

The other objective of the present invention is to provide a fluid dispensing or feeding device including an improved structure or mechanism for effectively pumping or pressurizing and feeding or injecting the fluid into the user.

In accordance with one aspect of the invention, there is provided a fluid dispensing device comprising a bottle for receiving fluid therein, a discharge tube, a pressurizing device coupled between the bottle and the discharge tube for pressurizing the fluid and for forcing the fluid to flow through the discharge tube without gravity, the pressurizing device including: a container coupled between the bottle and the discharge tube, a base member disposed in the container, a housing slidably engaged in the container and movable toward and away from the base member, the housing including a compartment formed therein for receiving the fluid, and an exit port provided in a bottom portion of the housing and communicating with the compartment of the housing for controlling the fluid to flow out of the compartment of the housing, a spring biased plug engaged between the base member and the housing for selectively engaging with the exit port of the housing and for controlling the fluid to flow out of the compartment of the housing, a cap mounted on top of the housing and moved in concert with the housing relative to the base member and the container, the cap including an orifice formed therein, a casing disposed in the compartment of the housing and attached to the cap and moved in concert with the cap and the housing relative to the base member and to the container, a spring biased valve piece engaged in the casing for selectively engaging with and blocking the orifice of the cap and for controlling the fluid to flow through the cap, a magnetic member attached to the casing and moved in concert with the cap and the casing and the housing relative to the base member and to the container, and a coil attached to the container to act with the magnetic member and to move the magnetic member and the casing and the cap and the housing in a reciprocating action within the container, and the spring biased plug being forced to move away from the exit port of the housing and to control the fluid to flow out of the compartment of the housing when the housing is moved toward the base member, and the spring biased valve piece being forced to move away from the orifice of the cap and for allowing the fluid to flow through the orifice of the cap and to flow into the casing and the housing when the housing is moved away from the base member.

The cap includes a gasket engaged into the orifice of the cap, and the gasket includes a passage formed therein for engaging with the spring biased valve piece. The cap includes a lock attached to the gasket and engaged with the cap for securing the gasket and the lock to the cap.

The magnetic member is attached to a bracket, and the bracket is attached or secured to the casing. The bracket includes at least one slot formed therein for defining at least one finger and for detachably securing the bracket and the magnetic member to the casing and for allowing the fluid to flow through the slot of the bracket.

The container includes a partition provided in the middle portion of the container for engaging with the base member, and the partition includes a hole formed therein for allowing the fluid to flow through the hole of the partition and then to flow out of the compartment of the housing.

The base member includes at least one cavity formed therein, and the housing includes at least one pin extended therefrom for engaging with the cavity of the base member and for slidably anchoring the housing to the base member and for guiding the housing to move relative to the base member.

The pressurizing device includes a receptacle having a chamber formed therein for receiving the container and for mounting onto the container, the coil is attached to the receptacle. A battery may further be provided and attached to the receptacle for energizing the coil.

The container includes a hollow hypodermic needle provided on an upper portion of the container for engaging into the bottle and for receiving the fluid from the bottle, the hollow hypodermic needle includes a flap extended therefrom, and the receptacle includes at least one catch provided thereon for engaging with the flap of the hollow hypodermic needle.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
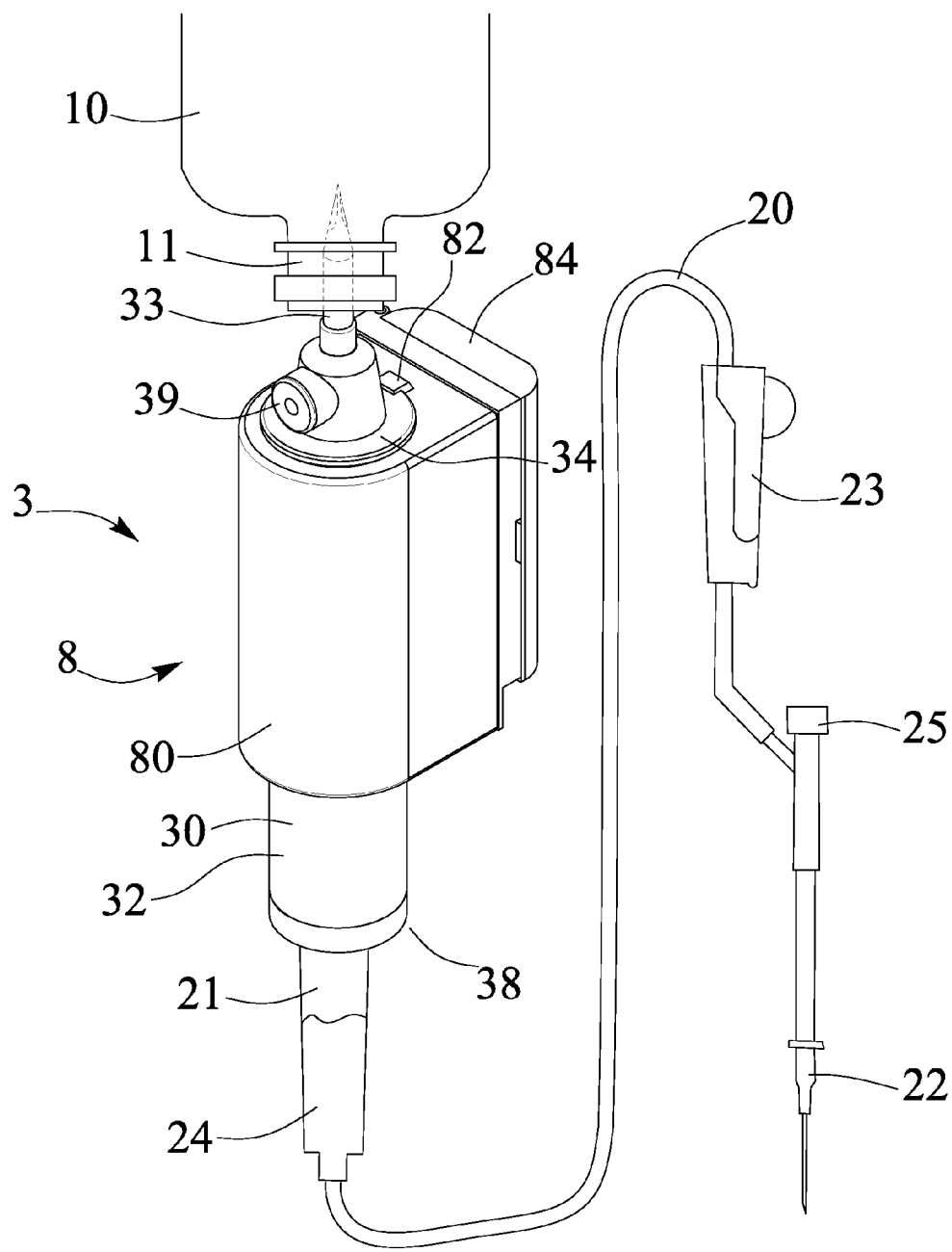
FIG. 1 is a partial perspective view of a fluid dispensing or feeding device in accordance with the present invention.

Referring to the drawings, and initially to FIGS. 1-4, a fluid dispensing or feeding device in accordance with the present invention comprises a fluid container or bottle 10 for receiving fluids, such as medicinal fluids to be fed or injected intravenously into human body tissue, and a delivery or discharge tube 20 having a hollow hypodermic needle 21 provided on one end thereof for coupling to the bottle 10, and having an injection needle 22 provided on the other end thereof, for penetrating into patient's body tissue and for the purposes of injecting the fluid as desired. A clamp valve 23 is attached onto the flexible discharge tube 20 so as to control the dispensing or the rate of flow of the fluid in the well known manner. Also positioned in the discharge tube 20 and located near the hollow hypodermic needle 21 or the bottle 10 is a drip meter or flow indicating device 24 usually made of transparent material for allowing the drops of fluid passing from the bottle 10 to the discharge tube 20 to be observed.

An injection mouth or air relief valve 25 may further be provided and attached to the discharge tube 20, and preferably disposed close to the injection needle 22, for selectively relieving air, and for preventing air from being injected into human body tissue inadvertently, when no fluid is forced to flow through the discharge tube 20; and/or for injecting or introducing the other medicinal fluids to be fed or injected or introduced into the injection needle 22 and then into the patient's body. The above-described structure or configuration for the fluid containing bottle 10 and the discharge tube 20 and the clamp valve 23 and the flow indicating device 24 and the injection mouth or air relief valve 25 is typical and is not related to the present invention and will not be described in further details.

Figure 2:
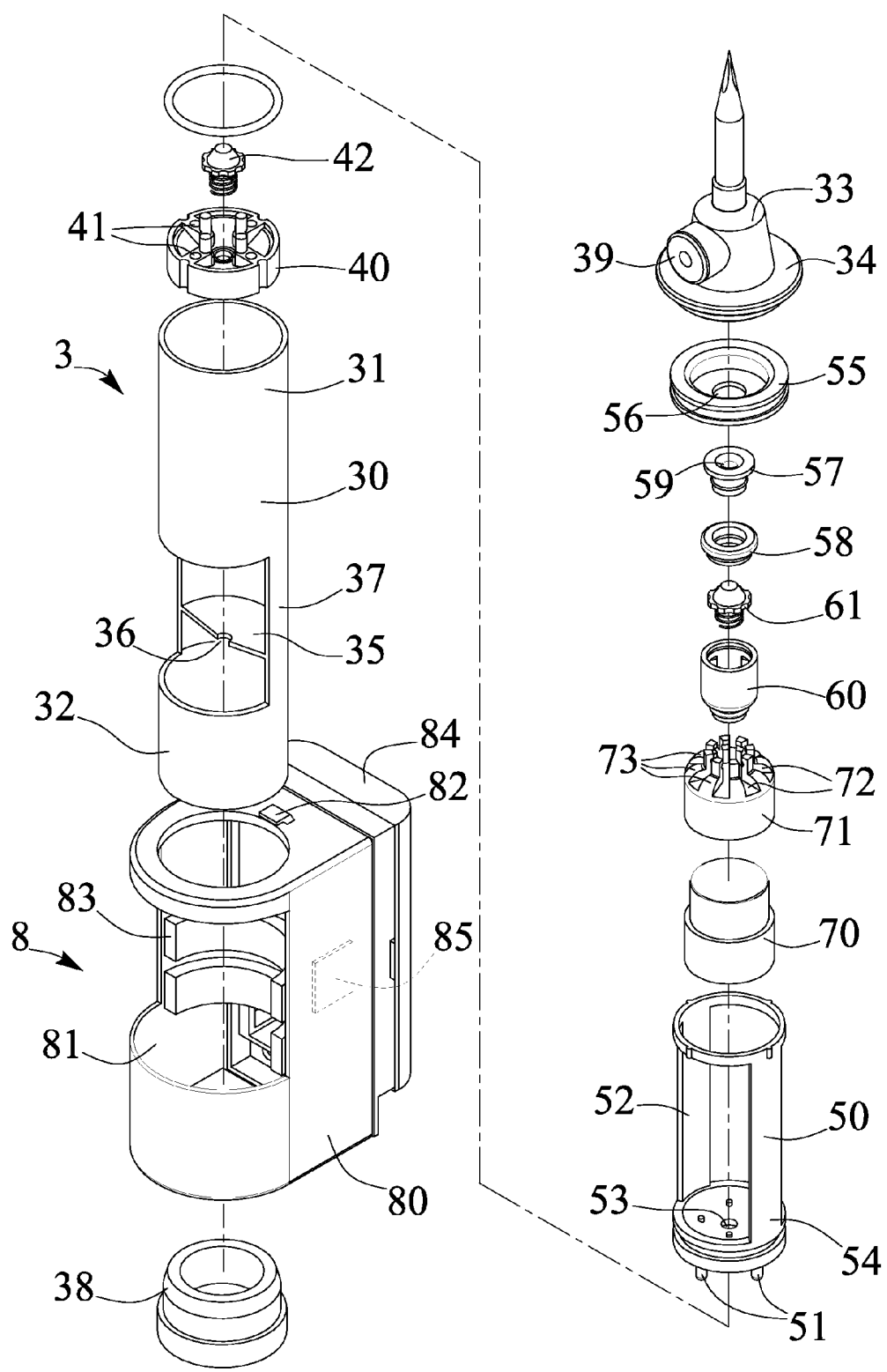
FIG. 2 is a partial exploded view of the fluid dispensing or feeding device.
Figure 3:
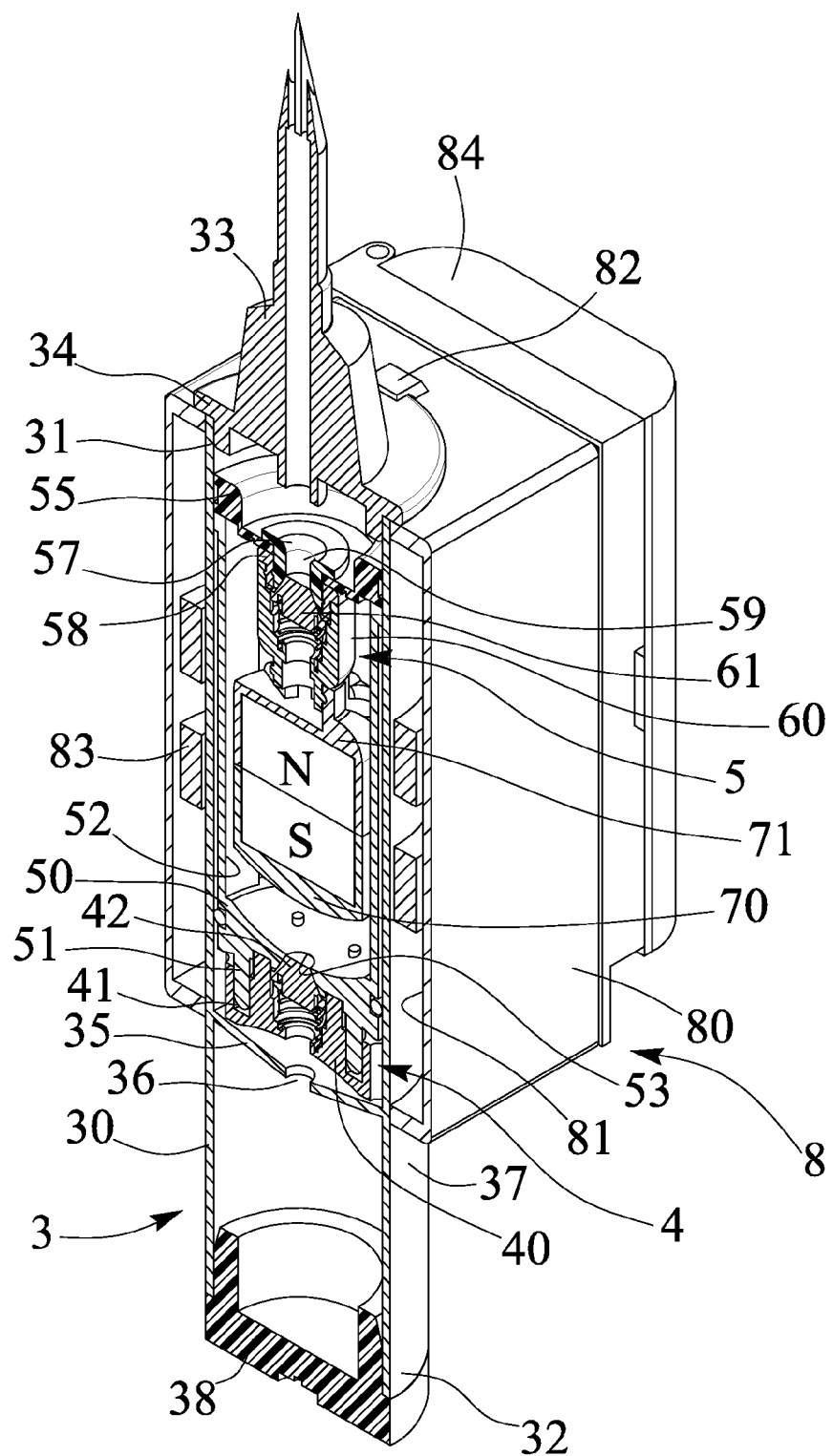
FIG. 3 is another partial perspective view of the fluid dispensing or feeding device, in which a portion of the fluid dispensing or feeding device has been cut off for showing the inner structure of the fluid dispensing or feeding device.
Figure 4:
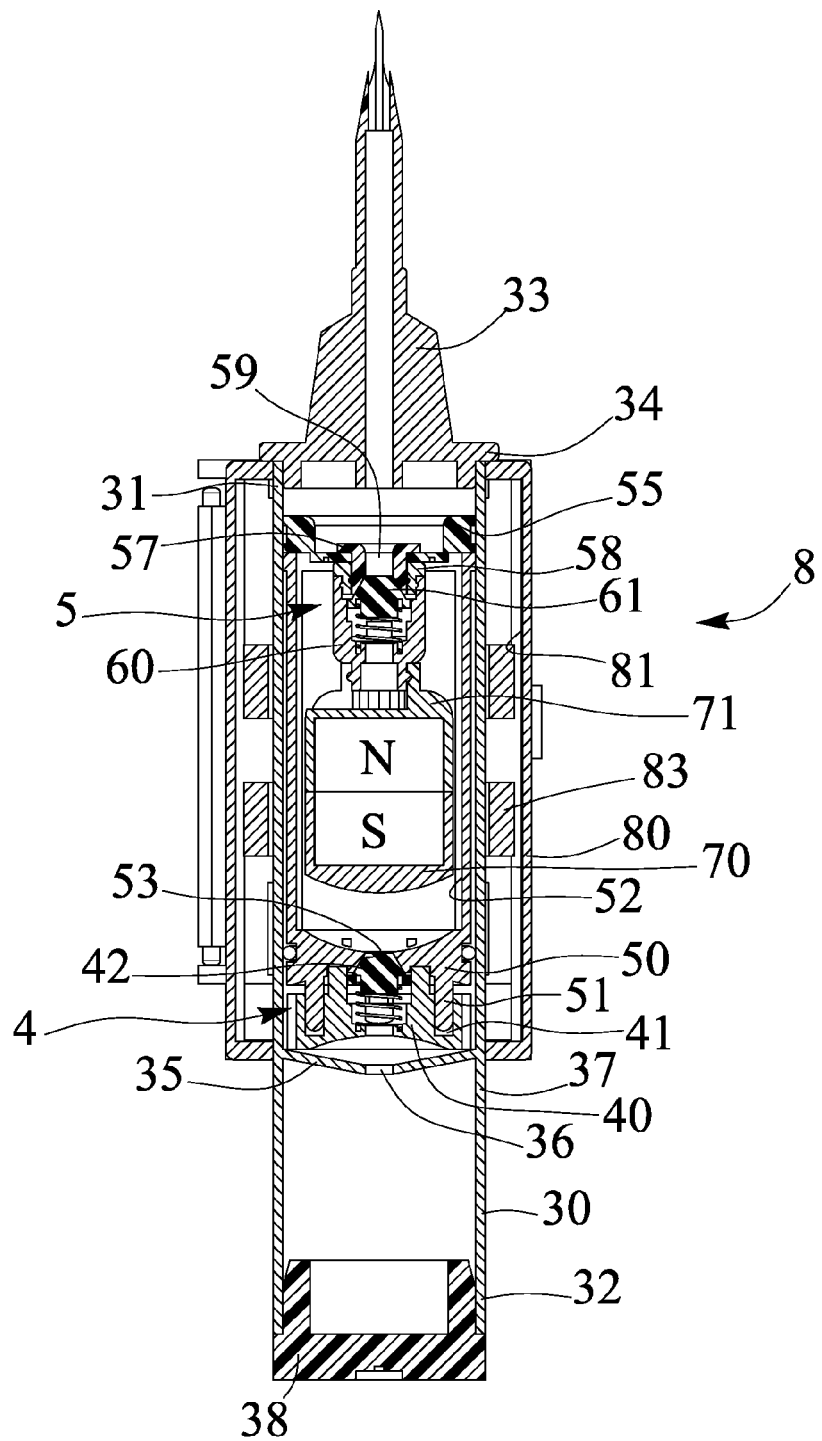
FIG. 4 is a partial cross sectional view of the fluid dispensing or feeding device as seen from the fluid dispensing or feeding device as shown in FIG. 3.

The fluid dispensing or feeding device includes a pressurizing device 3 attached to or coupled between the bottle 10 and the discharge tube 20, for pressurizing the fluid and for allowing the fluid to flow through the discharge tube 20 despite of the gravity, and thus for allowing the fluid bottle 10 to be disposed below the hearts of the patients or users, and thus for allowing the fluid dispensing or feeding device to be easily carried by the patients or users at any suitable position. As shown in FIGS. 2-4, the pressurizing means or device 3 includes a receptacle or container 30 having one or first end or upper portion 31 and another or second end or lower portion 32, and includes a hollow hypodermic needle 33 provided on or attached or mounted or secured onto the first end or upper portion 31 of the container 30 with such as a force-fitted engagement, a welder, an adhesive material or the like, for engaging into the lower or bottom neck portion 11 of the bottle 10, and thus for receiving the fluid from the bottle 10. The hollow hypodermic needle 33 includes a flange or flap 34 extended laterally and outwardly therefrom, and includes an air relief port 39 formed therein.

The container 30 includes a wall or partition 35 formed or provided in the other or second end or lower portion 32 or in the middle or intermediate portion 37 of the container 30, and the partition 35 includes a hole 36 formed therein for allowing the fluid to flow through the hole 36 of the partition 35 selectively. The container 30 further includes a resilient cover 38 attached to the bottom or lower portion 32 thereof, for blocking or enclosing the other end or lower portion 32 of the container 30. The hollow hypodermic needle 21 of the discharge tube 20 is to be engaged through the resilient cover 38 and into the container 30, for allowing the fluid to flow out of the fluid container 30 through the discharge tube 20. The resilient cover 38 is preferably made of such as rubber or synthetic materials for resiliently clamping or engaging with the hollow hypodermic needle 21 and for making a water tight seal between the fluid container 30 and the hollow hypodermic needle 21.

A first or lower check valve 4 includes a supporting seat or base member 40 disposed or engaged into the container 30 and seated or supported on the partition 35, and a housing 50 is slidably disposed or engaged into the container 30 and movable toward or away from the base member 40, the housing 50 may include one or more keys or projections or pegs or pins 51 extended therefrom for engaging with the corresponding holes or cavities 41 of the base member 40 and for slidably anchoring or retaining or positioning the housing 50 to the base member 40 and to the container 30 and for guiding the housing 50 to move up and down relative to the base member 40 and to the container 30. The housing 50 includes a chamber or compartment 52 formed therein for receiving the fluid, and a valve seat or exit port 53 formed or provided in the lower or bottom portion 54 thereof and communicating with the compartment 52 of the housing 50 for limiting or controlling the fluid to flow out of the compartment 52 of the housing 50.

A spring biased projection or plug 42 is disposed or attached or mounted or engaged onto the base member 40, or disposed or engaged between the base member 40 and the housing 50, for selectively engaging with the housing 50, and particularly for selectively engaging with the valve seat or exit port 53 of the housing 50 and for controlling the fluid to flow out of the compartment 52 of the housing 50. For example, when the housing 50 is moved downwardly toward the base member 40, the fluid contained in the compartment 52 of the housing 50 may force the spring biased plug 42 to be separated or disengaged from the valve seat or exit port 53 of the housing 50 (FIG. 5) in order to force the fluid to flow out of the compartment 52 of the housing 50 and to flow through the base member 40 and then to flow through the hole 36 of the partition 35 and to flow into the hollow hypodermic needle 21. The base member 40 and the valve seat or exit port 53 in the housing 50 and the spring biased plug 42 may thus form the first or lower check valve 4.

A second or upper check valve 5 includes another cover or cap 55 attached or mounted or engaged on top of the housing 50 and solidly and stably secured to the housing 50 with such as a force-fitted engagement, a welder, an adhesive material or the like, for allowing the cap 55 to be moved in concert with the housing 50 relative to the base member 40 and to the container 30. The cap 55 includes one or more orifices 56 formed therein (FIG. 2), another plug or valve seat or gasket 57 is engaged into the orifice 56 of the cap 55 and engaged onto the upper portion of the cap 55, and a fastener or lock 58 is attached or mounted or engaged onto the gasket 57 and contacted or engaged with the lower portion of the cap 55 for solidly and stably securing or anchoring or retaining the gasket 57 and the lock 58 to the cap 55, and the gasket 57 includes an aperture or passage 59 formed therein for allowing the fluid to flow through the cap 55.

A casing 60 is disposed in the compartment 52 of the housing 50 and attached or mounted or engaged with or secured onto the cap 55 and/or the gasket 57 and/or the lock 58 and moved in concert with the cap 55 and the housing 50 relative to the base member 40 and to the container 30, another spring biased projection or plug or valve piece 61 is disposed or engaged in the casing 60 and contacted or engaged with the gasket 57 and/or the cap 55 for selectively engaging with or blocking the passage 59 of the gasket 57 and for controlling the fluid to flow through the cap 55 and/or the gasket 57. A core 70, such as a magnetic member 70 is attached or mounted or secured to the cap 55 and/or the casing 60 and moved in concert with the cap 55 and the housing 50 relative to the base member 40 and to the container 30, for example, the core or magnetic member 70 is secured to the cap 55 or the casing 60 with another casing or frame or receptacle or bracket 71 which is attached or mounted or secured to the casing 60.

As best shown in FIG. 2, the bracket 71 includes one or more slits or slots 72 formed in the upper portion thereof for forming or defining one or more pawls or fingers 73 and for detachably or removably grasping or gripping or attaching or mounting or securing the bracket 71 and thus the core or magnetic member 70 to the casing 60 and/or the cap 55. As shown in FIG. 4, the fluid may selectively flow through the orifice 56 of the cap 55 and/or the passage 59 of the gasket 57 and may selectively flow into the casing 60 and may selectively flow out of the casing 60 through the slots 72 of the bracket 71, and may then selectively flow into the compartment 52 of the housing 50, and may then selectively flow out through the valve seat or exit port 53 of the housing 50. It is to be noted that the core or magnetic member 70 and the bracket 71 and the casing 60 and the cap 55 are secured to the housing 50 and moved in concert with the housing 50 relative to the base member 40 and to the container 30.

The pressurizing device 3 further includes an actuating device 8 having a receptacle 80, the receptacle 80 includes a compartment or chamber 81 formed therein for receiving the container 30 and for attaching or mounting or securing or engaging onto the container 30, for example, the receptacle 80 includes one or more (such as two) ears or catches 82 formed or provided thereon for engaging with the hollow hypodermic needle 33, and particularly the flap 34 of the hollow hypodermic needle 33 and for solidly and stably securing or anchoring or retaining the hollow hypodermic needle 33 and the receptacle 80 to the container 30, one or more coils 83 are provided and attached to the receptacle 80, such as attached to the middle portion of the receptacle 80 and disposed or supported or arranged around the core or magnetic member 70.

The pressurizing device 3 further includes one or more batteries 84 provided and attached or mounted or secured or coupled to the receptacle 80 in order to energize and actuate the coil 83 and so as to act with the core or magnetic member 70 and for allowing the core or magnetic member 70 and the housing 50 to be moved up and down relative to the container 30 and to be moved or driven in a reciprocating action within the container 30 by the action between the coil 83 and the magnetic members 70. The pressurizing device 3 may further include a circuit board or processor or control device 85 provided and attached or mounted or secured or coupled to the receptacle 80 for controlling or actuating or operating the coil 83 to act with the core or magnetic member 70 and to pump the fluid to flow from the hollow hypodermic needle 33 toward the cover 38 and the hollow hypodermic needle 21 and the discharge tube 20.

Figure 5:
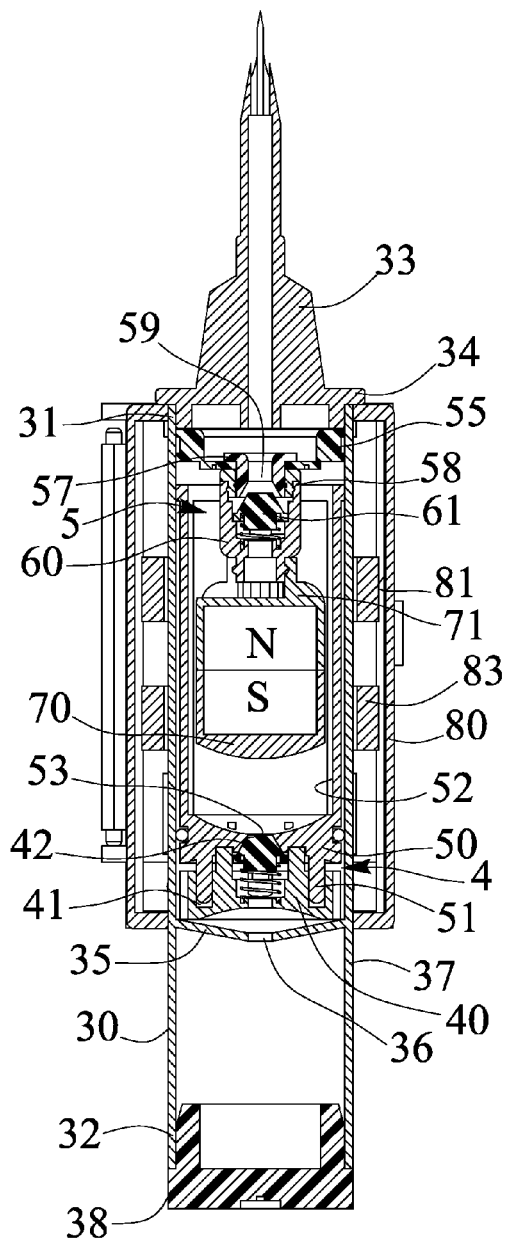
FIGS. 5, 6 are partial cross sectional views similar to FIG. 4, illustrating the operation of the fluid dispensing or feeding device.
Figure 6:
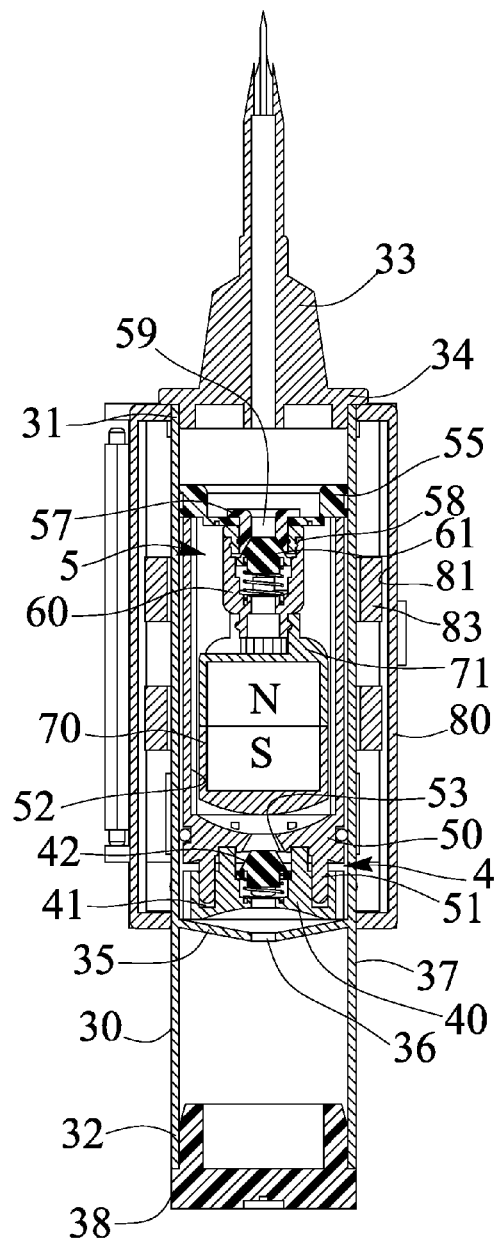

In operation, as shown in FIG. 5, when the magnetic member 70 and the housing 50 are moved or driven toward the base member 40 and the partition 35 and the cover 38 or away from the hollow hypodermic needle 33 by the coil 83 and the magnetic member 70, the fluid contained in the compartment 52 of the housing 50 may force the spring biased plug 42 to move away from the valve seat or exit port 53 of the housing 50 and may force the fluid to flow out of the compartment 52 of the housing 50 and to flow through the base member 40 and then to flow through the hole 36 of the partition 35 and to flow into the hollow hypodermic needle 21, such that the fluid may be pressurized by the coil 83 and the magnetic member 70 and the movement of the housing 50 relative to the container 30 and may be forced to flow through the discharge tube 20 without gravity, such that the fluid bottle 10 may be disposed below the hearts of the patients or users, and such that the fluid dispensing or feeding device may be easily carried by the patients or users without worrying about the gravity force.

On the contrary, when the magnetic member 70 and the housing 50 are moved or driven away from the base member 40 and the partition 35 and the cover 38 or toward the hollow hypodermic needle 33 by the coil 83 and the magnetic member 70, the spring biased plug 42 may be biased and moved to engage with and to block the valve seat or exit port 53 of the housing 50, and the fluid contained in the upper portion 31 of the container 30 may force the spring biased valve piece 61 to move away from the gasket 57 and/or the cap 55 and may flow into the casing 60 and may selectively flow out of the casing 60 through the slots 72 of the bracket 71, and may then selectively flow into the compartment 52 of the housing 50 and contained in the compartment 52 of the housing 50 and wait to be forced to selectively flow out through the discharge tube 20 again when the magnetic member 70 and the housing 50 are moved or driven toward the base member 40 and the partition 35 and the cover 38 or away from the hollow hypodermic needle 33 by the coil 83 and the magnetic member 70 again. The casing 60 and the cap 55 and/or the gasket 57 and/or the lock 58 and the spring biased valve piece 61 may thus form the second or upper check valve 5.

Accordingly, the fluid may be pressurized by the coil 83 and the magnetic member 70 in a reciprocating action, and may be controlled and forced to flow through the discharge tube 20 without gravity. The coil 83 and the magnetic member 70 and the housing 50 and/or the flow indicating device 24 may be suitably arranged to control the dispensing or the rate of flow of the fluid through the discharge tube 20, and to prevent the fluid from being over pressurized. The coil 83 and the magnetic member 70 may be controlled or actuated by a switch (not shown) or the like. The other control device 85 may be used to control or to adjust or to change the operating speed of the coil 83 and the magnetic member 70 and/or the rate of flow of the medicine fluid into the patient's body tissue.

Accordingly, the fluid dispensing or feeding device in accordance with the present invention includes a pressurizing device for pressurizing the fluid and for allowing the fluid bottle to be disposed below hearts of patients or users, and thus for allowing the fluid dispensing or feeding device to be easily carried by the patients or users, and includes an improved structure or mechanism for effectively pumping or pressurizing and feeding or injecting the fluid into the user.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A fluid dispensing device comprising:
    a bottle for receiving fluid therein,
    a discharge tube,
    a pressurizing device coupled between said bottle and said discharge tube for pressurizing the fluid and for forcing the fluid to flow through said discharge tube without gravity, said pressurizing device including:
        a container coupled between said bottle and said discharge tube,
        a base member disposed in said container,
        a housing slidably engaged in said container and movable toward and away from said base member, said housing including a compartment formed therein for receiving the fluid, and an exit port provided in a bottom portion of said housing and communicating with said compartment of said housing for controlling the fluid to flow out of said compartment of said housing,
        a spring biased plug engaged between said base member and said housing for selectively engaging with said exit port of said housing and for controlling the fluid to flow out of said compartment of said housing,
        a cap mounted on top of said housing and moved in concert with said housing relative to said base member and said container, said cap including an orifice formed therein,
        a casing disposed in said compartment of said housing and attached to said cap and moved in concert with said cap and said housing relative to said base member and to said container,
        a spring biased valve piece engaged in said casing for selectively engaging with and blocking said orifice of said cap and for controlling the fluid to flow through said cap,
        a magnetic member attached to said casing and moved in concert with said cap and said casing and said housing relative to said base member and to said container, and
        at least one coil attached to said container to act with said magnetic member and to move said magnetic member and said casing and said cap and said housing in a reciprocating action within said container, and
        said spring biased plug being forced to move away from said exit port of said housing and to control the fluid to flow out of said compartment of said housing when said housing is moved toward said base member, and said spring biased valve piece being forced to move away from said orifice of said cap and for allowing the fluid to flow through said orifice of said cap and to flow into said casing and said housing when said housing is moved away from said base member.

2. The fluid dispensing device as claimed in claim 1, wherein said cap includes a gasket engaged into said orifice of said cap, and said gasket includes a passage formed therein for engaging with said spring biased valve piece.

3. The fluid dispensing device as claimed in claim 2, wherein said cap includes a lock attached to said gasket and engaged with said cap for securing said gasket and said lock to said cap.

4. The fluid dispensing device as claimed in claim 1, wherein said magnetic member is attached to a bracket, and said bracket is secured to said casing.

5. The fluid dispensing device as claimed in claim 4, wherein said bracket includes at least one slot formed therein for defining at least one finger and for detachably securing said bracket and said magnetic member to said casing.

6. The fluid dispensing device as claimed in claim 1, wherein said container includes a partition provided in said container for engaging with said base member, and said partition includes a hole formed therein for allowing the fluid to flow through said hole of said partition.

7. The fluid dispensing device as claimed in claim 1, wherein said base member includes at least one cavity formed therein, and said housing includes at least one pin extended therefrom for engaging with said at least one cavity of said base member and for slidably anchoring said housing to said base member and for guiding said housing to move relative to said base member.

8. The fluid dispensing device as claimed in claim 1, wherein said pressurizing device includes a receptacle having a chamber formed therein for receiving said container and for mounting onto said container, said at least one coil is attached to said receptacle.

9. The fluid dispensing device as claimed in claim 8, wherein said container includes a hollow hypodermic needle provided on an upper portion of said container for engaging into said bottle and for receiving the fluid from said bottle, said hollow hypodermic needle includes a flap extended therefrom, and said receptacle includes at least one catch provided thereon for engaging with said flap of said hollow hypodermic needle.

10. The fluid dispensing device as claimed in claim 8, wherein a battery is attached to said receptacle.

* * * * *